(12) United States Patent
Hoheisel

(10) Patent No.: US 7,290,930 B2
(45) Date of Patent: Nov. 6, 2007

(54) METHOD FOR MONITORING AN X-RAY APPARATUS AND X-RAY APPARATUS

(75) Inventor: Martin Hoheisel, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 11/432,242

(22) Filed: May 11, 2006

(65) Prior Publication Data

US 2007/0140429 A1 Jun. 21, 2007

(30) Foreign Application Priority Data

May 12, 2005 (DE) .................. 10 2005 022 108

(51) Int. Cl.
*A61B 6/08* (2006.01)
(52) U.S. Cl. ...................... 378/206; 378/205
(58) Field of Classification Search ............... 378/62, 378/64, 108, 117, 193, 197, 204–206
See application file for complete search history.

(56) References Cited

U.S. PATENT DOCUMENTS 7,046,765 B2 * 5/2006 Wong et al. ................ 378/117
2005/0013407 A1 1/2005 Scheuering 2005/0059877 A1 * 3/2005 Falbo, Sr. ................... 600/407

FOREIGN PATENT DOCUMENTS

DE 101 18 183 A1 11/2002
EP 0 559 120 B1 9/1993

OTHER PUBLICATIONS

U.S. Food and Drug Administration; "FDA Public Healt Advisory: Avoidance of Serious X-Ray-Induced Skin Injuries to patients During Fluoroscopically-Guided Procedures"; Sep. 30, 1994; [Retrieved from internet on] May 9, 2006; [Retrieved from] http://www.fda.gov/cdrh/fluor.html.
U.S. Food and Drug Administration; "Recording Information in the Patient's Medical Record that Identifies the Potential for Serious X-Ray-Induced Skin Injuries"; Sep. 15, 1995; [Retrieved from Internet on] May 9, 2006; [Retrieved from] http://www.fda.gov/cdrh/xrayinj.html.

* cited by examiner

*Primary Examiner*—Edward J. Glick
*Assistant Examiner*—Irakli Kiknadze

(57) ABSTRACT

The invention relates to a method for monitoring an x-ray apparatus. To prevent the application of a harmful x-ray dose, it is proposed in accordance with the invention to compare a distance value indicating a distance between an x-ray source and a surface of a patient with a predetermined mini-mum distance value and to generate a warning signal, if the distance value is smaller than the minimum distance value.

17 Claims, 1 Drawing Sheet

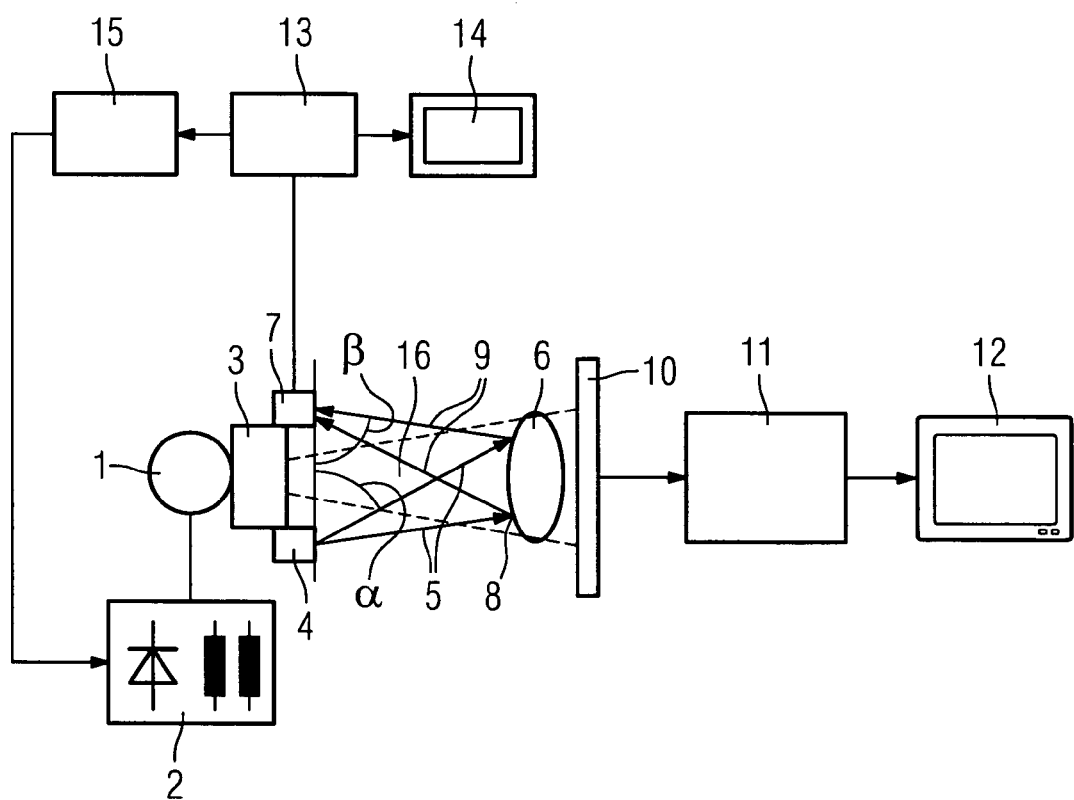

METHOD FOR MONITORING AN X-RAY APPARATUS AND X-RAY APPARATUS

CROSS REFERENCE TO RELATED APPLICATIONS

This application claims priority to the German Application No. 10 2005 022 108.4, filed May 12, 2005 which is incorporated by reference herein in its entirety.

FIELD OF INVENTION

The invention relates to a method for monitoring an x-ray apparatus as well as an x-ray apparatus.

BACKGROUND OF INVENTION

With conventional x-ray apparatuses for medical applications, a distance from an x-ray source can be manually adjusted. If only a minimum distance between the x-ray source and the patient is selected at the same time as an excessively large dose, this may lead to radiation injury to the skin of the patient.

DE 101 18 183 A1 describes an x-ray device with an apparatus for measuring a distance between an x-ray source and a surface of a patient. The distance is measured from a delay time difference of a laser beam. A thickness of the patient is finally determined from the measured distance on the basis of a previously known distance to a patient support. The device operating parameters are then automatically adjusted on the basis of the determined thickness. The proposed apparatus requires the provision of a light source, which is particularly suited to emitting short light impulses or to emitting amplitude—modulated light. Provision is to be further made for a light receiver, which enables a time resolution in the picosecond, subnanosecond or nanosecond range. The proposed apparatus is generally complex to manufacture. As the device operating parameters and thus the x-ray dose are only adjusted on the basis of the thickness, an inadmissibly high radiation load on the surface of a patient can not always be safely avoided.

US 2005/0013407 A1 describes an x-ray device, in which a laser distance measuring facility is likewise provided to measure a distance between an x-ray source and a patient. In this way, a thickness of the patient to be examined is in turn calculated from the measured distance. A radiation dose is determined as a function of the result thereby achieved. An x-ray dose determined solely on the basis of a thickness of the patient can, in the case of an excessively short distance between the x -ray source and the patient, result in radiation injury to the skin of the patient.

SUMMARY OF INVENTION

An object of the invention is to eliminate the disadvantages according to the prior art. In particular, a method and an x-ray apparatus are to be specified, with which the application of an inadmissibly high x-ray dose can be avoided in a safe and reliable manner.

This object is achieved by the claims.

In accordance with the invention, provision is made for a method for monitoring an x-ray apparatus having a generator for supplying an x-ray source with high voltage and an optical distance measuring facility provided on the x-ray source, with the method comprising the following steps:

Measuring a distance between the x-ray source and a surface of a patient facing the x-ray source using the distance measuring facility, Comparing a measured distance value with a predetermined minimum distance value, and Generating a signal, if the measured distance value is smaller than the minimum distance value.

As, in accordance with the invention, a signal is generated when a predetermined minimum distance value is not reached, the application of an inadmissibly high skin dose can be safely and reliably avoided. In terms of the present invention, "Generating a signal" is generally understood to mean a change in state which can be detected using electrical or electronic means and can be used for switching purposes. In other words, the "Generating a signal" can be both the switching on and switching off of a signal describing a state.

According to an advantageous embodiment of the invention, a light measuring facility, preferably a laser measuring facility is used as the distance measuring facility. The distance value can be advantageously determined from an entry angle of laser light reflected at the surface of the patient. "Entry angle" is understood here to mean an angle, at which a light reflected by the surface of the patient enters a light detection facility, a camera or suchlike for instance. Provided a radiation angle of the light generated by a light source is known, the distance value can be concluded from the radiation angle and the entry angle. Such a determination of the distance value according to the conventionally known triangulation method enables a particularly simple and cost-effective design of the laser measuring facility. A conventional CCD camera can be used to receive the reflected laser light for instance. Reference is made in this respect to EP 0 559 120 B1 for instance. The term "skin dose" refers to a dose at the entry point into the patient.

According to a particularly advantageous embodiment, provision is made for a warning signal and/or a cut-off signal to be produced as a signal to cut off the generator. In the event that the minimum distance value is not reached, an application of an undesirably high dose can be avoided in a safe and reliable manner.

The measured and/or minimum distance value can be displayed by means of a display apparatus. This allows a manual adjustment of a suitable distance between the x-ray source and the surface of the patient.

According to a particularly advantageous embodiment, provision is made for the minimum distance value to be automatically calculated by means of a data processing facility on the basis of a predetermined calculation specification and using parameters, which are relevant for a skin dose of the x-rays to be applied. The parameters can be operating parameters of the x-ray source, in particular an x-ray voltage, an x-ray current, parameters relating to filtering and suchlike. By way of example, the minimum distance value can be dynamically recalculated in each instance as a function of the size of an x-ray exposure to be produced and can be compared with the measured distance value.

According to a further embodiment of the invention, an applied x-ray dose is automatically recorded by means of the data processing facility. This allows the treating doctor to determine immediately whether and optionally with which x-ray dose the patient has been treated in the past. An examination and/or therapy by means of an x -ray apparatus can be adapted thereto.

According to a further embodiment, provision is made for the distance values to be measured in a region of the surface which can be illuminated with a light source and which displays a radiation surface of the x-rays. To this end, the distance measuring facility can be affixed to a diaphragm facility of the x-ray apparatus. It has proven particularly advantageous, in terms of applying a laser beam generated with a laser measuring facility, to use the optical beam path of the light source for the purpose of illuminating a radiation surface of the x-rays. In this case, the light or laser beam used for distance measurement is always located within the radiation surface of the light source.

In accordance with the invention, provision is made for an x-ray apparatus with a generator for supplying an x-ray source with high voltage and an optical distance measuring facility provided on the x-ray source, with a monitoring facility being provided to compare the measured distance value with a predetermined minimum distance value and a facility for generating a signal, if the measured distance value is smaller than the minimum distance value.

The monitoring facility can be a process computer-aided facility, a computer for instance, which can be programmed. A comparison value determined herewith can be transmitted to the facility for generating a signal. The facility for generating a signal allows a signal indicating that the minimum distance value has not been reached or has been exceeded to be generated, as a function of the supplied comparison value.

According to a further embodiment of the invention, a data processing facility is provided for determining the distance value from a detection angle of the laser light reflected at the surface of the patient. The minimum distance value can be automatically calculated by means of the data processing facility on the basis of a predetermined calculation specification and using parameters, which are relevant for a skin dose of the x-rays to be applied.

According to a further embodiment, provision is made for an applied skin dose to be automatically recorded by means of the data processing facility.

Several receivers, in particular CCD cameras can be provided to detect the light beam or laser beam reflected by the surface of the patient. This allows improved measurement accuracy. In particular, a distance measurement is then still possible, even if a reflected light beam or laser beam can not be detected with one of the cameras as a result of an occlusion of the beam path.

For further advantageous embodiments of the x-ray apparatus, reference is made to the preceding embodiments of the method. The definitions, features and advantages described there also apply correspondingly to the x-ray apparatus.

BRIEF DESCRIPTION OF THE DRAWING

The invention is described in more detail below with reference to an exemplary embodiment.

DETAILED DESCRIPTION OF INVENTION

In the only figure, a high voltage generator 2 is provided to supply an x-ray source 1 with high voltage. Provision is made on a diaphragm 3 for a laser source 4 for applying laser beams 5 to a surface of a patient 6 and for at least one camera 7 for detecting laser beams 9 reflected in the light spots 8. An x-ray detector is identified with reference character 10, an image processing unit 11 and a monitor 12 being arranged downstream thereof. A data processing facility 13 serves to evaluate the signals supplied by the camera 7. A distance value determined in this way can be displayed by means of a display apparatus 14. A monitoring facility comprising a signal generating facility is identified with reference character 15, said monitoring facility being connected in turn to the high voltage generator 2.

The function of the apparatus is as follows:

A surface of the patient 6 facing the x-ray source 3 is radiated by means of the laser source 4. The laser beams 9 reflected by the surface are detected by the camera 7 at an entry angle $\alpha$. On the basis of the detected entry angle $\alpha$ and a radiation angle $\beta$, a distance between the x-ray source 1 and the surface of the patient 6 can subsequently be determined on the basis of the triangulation method using the data processing facility 13. The determined distance value can be displayed on the display apparatus 14.

The determined distance value is forwarded to the monitoring facility 15 and compared there with a minimum distance value. The minimum distance value can be permanently preset. It can however also be calculated dynamically on the basis of a predetermined calculation specification. To calculate the minimum distance value, parameters can be taken into consideration, which are relevant for the skin dose of the x-rays to be applied. These can be parameters such as tube voltage, tube current, filtering, radiation time, the size of a radiation surface and suchlike. A minimum distance value is always calculated according to the predetermined calculation specification, such that the application of a harmful skin dose is avoided.

In the monitoring facility 15, the measured distance value is compared with the minimum distance value. A warning signal is output for instance by means of the display apparatus 14, if it is determined during the comparison that the measured distance value is smaller than the minimum distance value. At the same time, a current supply to the high voltage generator 2 can be interrupted.

An undesirable application of a harmful skin dose can thus be avoided in a simple and reliable manner.

The invention claimed is:

1. A method of monitoring an x-ray apparatus having a generator for supplying high voltage to an x-ray source, the x-ray source having an optical distance measuring device, the method comprising:
   determining a distance between the x-ray source and a surface of a patient facing the x-ray source, by the distance measuring device;
   calculating a predetermined minimum distance between the x-ray source and the surface of the patient facing the x-ray source, by a data processing unit based upon predetermined calculation rules and parameters for an x-ray dose to be applied to a skin of the patient;
   comparing the measured distance to the predetermined minimum distance; and
   generating a warning signal if the determined distance is smaller than the predetermined minimum distance.

2. The method according to claim 1, wherein the distance measuring device is a laser-based measuring device.

3. The method according to claim 1, wherein determining the distance includes determining an angle between the surface and light reflected from the surface, the light originating from the distance measuring device.

4. The method according to claim 1, further comprising shutting down the generator by the warning signal.

5. The method according to claim 1, further comprising displaying the determined or the prescribed minimum distance on a display.

6. The method according to claim 1, wherein the applied x-ray dose is automatically recorded by the data processing unit.

7. The method according to claim 1, wherein the distance is measured relative to an area of the surface illuminated by a light source.

8. The method according to claim 1, wherein the parameters are operating parameters of the x-ray source selected from the group consisting of: an x-ray voltage, an x-ray current, a filtering parameter, a radiation time, and a size of radiation surface.

9. The method according to claim 1, wherein the predetermined minimum distance is dynamically recalculated by the data processing unit as a function of an x-ray exposure to be produced.

10. An x-ray device, comprising:
a generator for supplying high voltage to an x-ray source;
an optical distance measuring device arranged on the x-ray source, the optical distance measuring device configured to determine a distance between the x-ray source and a surface of a patient facing the x-ray source;
a data processing unit for calculating a predetermined minimum distance between the x-ray source and the surface of the patient facing the x-ray source based upon predetermined calculation rules and parameters for an x-ray dose to be applied to a skin of the patient;
a monitoring unit configured comparing the determined distance to the predetermined minimum distance; and
a signal generator for generating a warning signal if the determined distance is smaller than the minimum predetermined distance value.

11. The x-ray device according to claim 10, wherein the distance measuring device is a laser-based measuring device.

12. The x-ray apparatus according to claim 11, further comprising a light source for illuminating an area of the surface to be exposed to x-rays, wherein a laser beam emitted from the laser-based measuring device hits the surface within the illuminated area.

13. The x-ray device according to claim 10, wherein determining the distance includes determining an angle between the surface and light reflected from the surface, the light originating from the distance measuring device.

14. The x-ray device according to claim 10, wherein the warning signal shuts down the generator.

15. The x-ray device according to claim 10, further comprising a display for displaying the determined or the prescribed minimum distance.

16. The x-ray device according to claim 10, wherein the data processing unit is further configured to record the applied x-ray dose.

17. The x-ray device according to claim 10, wherein the predetermined minimum distance is dynamically recalculated by the data processing unit as a function of an x-ray exposure to be produced.

* * * * *